(12) United States Patent
Degenhardt et al.

(10) Patent No.: US 9,029,166 B2
(45) Date of Patent: May 12, 2015

(54) METHOD OF IDENTIFYING NATURAL SUBSTANCES CAPABLE OF COMPLEXATION

(75) Inventors: Andreas Degenhardt, Holzminden (DE); Gerhard Krammer, Holzminden (DE); Nicole Schulze, Alfeld (DE)

(73) Assignee: Symrise AG, Holzminden (DE)

( * ) Notice: Subject to any disclaimer, the term of this patent is extended or adjusted under 35 U.S.C. 154(b) by 528 days.

(21) Appl. No.: 13/220,105

(22) Filed: Aug. 29, 2011

(65) Prior Publication Data
US 2012/0052589 A1     Mar. 1, 2012

Related U.S. Application Data

(60) Provisional application No. 61/378,587, filed on Aug. 31, 2010.

(51) Int. Cl.
*G01N 33/00* (2006.01)
*C07K 1/22* (2006.01)
*G01N 30/02* (2006.01)
*G01N 1/40* (2006.01)
*G01N 33/02* (2006.01)

(52) U.S. Cl.
CPC ............ *C07K 1/22* (2013.01); *G01N 2030/022* (2013.01); *G01N 33/00* (2013.01); *G01N 1/4077* (2013.01); *G01N 1/405* (2013.01); *G01N 33/0098* (2013.01); *G01N 33/025* (2013.01)

(58) Field of Classification Search
CPC .............. B01D 15/3828; G01N 30/00; G01N 2030/022; G01N 1/4077; G01N 1/405; G01N 33/0098; G01N 33/025; C07K 1/22
USPC ........................................................ 436/161
See application file for complete search history.

(56) References Cited

U.S. PATENT DOCUMENTS 7,456,276 B2 *   11/2008   Christensen et al. ...... 536/123.1

FOREIGN PATENT DOCUMENTS

WO   WO 2006111476 A1 *   10/2006   ............ G01N 30/88

OTHER PUBLICATIONS http://web.archive.org/web/20090425151449/http://www.merriam-webster.com/dictionary/elute.*
https://web.archive.org/web/20090403191710/http://en.wikipedia.org/wiki/Fast_protein_liquid_chromatography.*
Dimitri Heintz, Virginie Wurtz, Anthony A. High, Alain Van Dorsselaer, Ralf Reski, Eric Sarnighausen, Electrophoresis 2004, 25, 1149-1159.*
Avonce "The moss *Physcomitrella patens* as a green factory" was accessed by the examiner at https://lirias.kuleuven.be/handle/123456789/286016 on Mar. 24, 2014.*
Elizabeth Barker "An Examination of Leaf Morphogenesis in the Moss, *Physcomitrella patens*" A Thesis Aug. 2011 (http://ourspace.uregina.ca/handle/10294/3530).*
Nobuyuki Takeda, Tomofumi Matsuoka, Misao Gotoh, Chromatographia 2010, 72, July (No. 1/2) 127.*
Dimitri Heintz, Virginie Wurtz, Anthony A. High, Alain Van Dorsselaer, Ralf Reski, Eric Sarnighausen, An efficient protocol for the identification of protein phosphorylation in a seedless plant, sensitive enough to detect members of signalling cascades, Electrophoresis 2004, 25, 1149-1159.*
Todd J. Menkhaus, Yun Bai, Chenming Zhang, Zivko L. Nikolov, and Charles E. Glatz, Considerations for the Recovery of Recombinant Proteins from Plants, Biotechnol. Prog. 2004, 20, 1001-1014.*
Fernando M. Nunes and Manuel A. Coimbra "Melanoidins from Coffee Infusions. Fractionation, Chemical Characterization, and Effect of the Degree of Roast" J. Agric. Food Chem. 2007, 55, 3967-3977.*

* cited by examiner

*Primary Examiner* — Christopher A. Hixson
*Assistant Examiner* — Emily Berkeley
(74) *Attorney, Agent, or Firm* — Dilworth & Barrese, LLP

(57) ABSTRACT

The present invention relates to a method of identifying a natural substance that is capable of complexation with $Ni^{2+}$, $Cu^{2+}$ and/or $Fe^{2+}$ ions, wherein an extract containing natural substances is led over a stationary phase loaded with $Ni^{2+}$, $Cu^{2+}$ and/or $Fe^{2+}$ ions, which is suitable for immobilized metal affinity chromatography (IMAC).

16 Claims, No Drawings

METHOD OF IDENTIFYING NATURAL SUBSTANCES CAPABLE OF COMPLEXATION

CROSS REFERENCE TO RELATED APPLICATIONS

This application claims priority to U.S. Provisional Application No. 61/378,587, filed Aug. 31, 2010, which is incorporated herein by reference in its entirety.

The present invention relates to a method of identifying a natural substance that is capable of complexation with $Ni^{2+}$, $Cu^{2+}$ and/or $Fe^{2+}$ ions, wherein an extract containing natural substances is led over a stationary phase loaded with $Ni^{2+}$, $Cu^{2+}$ and/or $Fe^{2+}$ ions, which is suitable for immobilized metal affinity chromatography (IMAC). The invention further relates to the use of a stationary phase loaded with $Ni^{2+}$, $Cu^{2+}$ and/or $Fe^{2+}$ ions, which is suitable for immobilized metal affinity chromatography (IMAC), for identifying a natural substance that is capable of complexation with $Ni^{2+}$, $Cu^{2+}$ and/or $Fe^{2+}$ ions.

Flavoring compositions (often also called flavorings) contain at least two different substances with sensory action. Generally, however, flavorings are complex mixtures of a large number of components with sensory action. The substances with sensory action can be volatile (odors or aromas) or non-volatile (flavoring ingredients). The volatile aromas (aroma substances) can be perceived by humans via both the orthonasal and retronasal routes. The flavoring ingredients interact with the taste receptors of the tongue and are responsible for the gustatory (taste) impressions sweet, sour, bitter, salty and umami, but in addition other, often trigeminal stimuli are also perceived, for example sharp, burning, cooling, electrifying ("tingling") or prickling effects.

Foodstuffs within the scope of the present text are orally consumable preparations, which are intended to be placed in the human oral cavity, to remain there for a certain time and then either be consumed (e.g. foodstuffs ready for consumption, beverages) or to be removed from the oral cavity again (e.g. chewing gums).

Within the scope of the present text, "foodstuff" means in particular substances that are intended, in the unchanged, prepared or processed state, to be swallowed by a human and then digested; foodstuffs also include enrobings, coatings or other coverings, which are intended to be swallowed as well, or for which swallowing is to be expected. Certain products that are usually removed again from the oral cavity (e.g. chewing gums) are also to be understood as foodstuffs within the scope of the present text.

In the area of orally consumable preparations, in particular in the area of foodstuffs, flavor and taste stability is an important quality criterion. Orally consumable preparations, in particular foodstuffs, should produce a sensory impression that remains as constant as possible for as long as possible, and in particular should have a flavor and taste profile that is as constant as possible.

Oxidative degradation reactions of certain constituents of orally consumable preparations, in particular of foodstuffs, can often have the effect that the flavor and/or the taste changes over time, thus leading to sensory, in particular olfactory and/or gustatory, instability. These changes that are undesirable in sensory terms are known as flavor defects (off-notes, "off-flavor"). Traces of metal ions, in particular of $Ni^{2+}$, $Cu^{2+}$ and/or $Fe^{2+}$ ions, may in particular be involved in the corresponding oxidative degradation reactions.

In foods, volatile compounds can be formed by the oxidation of unsaturated substances, e.g. by lipid peroxidation, which have very low odor and taste thresholds, so that even at low concentration they produce undesirable notes in the flavor profiles of foods and can cause flavor defects. Such instabilities and flavor defects are known for example from the aroma and/or taste of oxidation-sensitive foods such as beer, dressings and margarines.

Up to now, antioxidants have often been used for sensory stabilization, for example ascorbic acid (vitamin C), ascorbates, tocopherols or BHT. These substances have antioxidative or reducing action.

Moreover, certain metal-ion-complexing compounds, for example calcium disodium ethylenediaminetetraacetate (E number 385), can be added to orally consumable preparations, in particular foodstuffs. However, the metal-ion-complexing action of EDTA and EDTA salts is too strong and they can withdraw metal ions from the human body undesirably, which is a drawback in particular in the case of $Fe^{2+}$ ions.

It would therefore be desirable to find substances that are orally consumable by humans and can complex metal ions, in particular $Ni^{2+}$, $Cu^{2+}$ and/or $Fe^{2+}$ ions, but complexing these metal ions less strongly than EDTA (ethylenediaminetetraacetic acid) or EDTA salts. Moreover, it would be advantageous if these substances were of natural origin, i.e. obtainable from natural sources.

The object to be achieved by the present invention was to provide a method of identifying natural substances that are consumable by humans, wherein said natural substances are suitable for increasing the sensory stability, in particular the olfactory and/or gustatory stability, of orally consumable preparations, in particular of foodstuffs.

These natural substances should in particular reduce or prevent the catalytic activity of any metal ions that are present and oxidative degradation reactions that lead to impairment of the sensory stability of orally consumable preparations. Preferably these natural substances should not be proteins with a molecular weight of 20 kDa or more.

The present invention therefore relates to a method of identifying a natural substance that is capable of complexation with $Ni^{2+}$, $Cu^{2+}$ and/or $Fe^{2+}$, characterized by the following steps:

(a) providing an aqueous, alcoholic or aqueous-alcoholic extract containing natural substances,
(b) providing a device containing a stationary phase loaded with $Ni^{2+}$, $Cu^{2+}$ and/or $Fe^{2+}$ ions, which is suitable for immobilized metal affinity chromatography (IMAC) (IMAC device),
(c) leading the extract containing natural substances from step (a) through a device from step (b), so that the natural substance capable of complexation with $Ni^{2+}$, $Cu^{2+}$ and/or $Fe^{2+}$ ions is adsorbed on the stationary phase of the IMAC device,
(d) optionally rinsing the stationary phase of the IMAC device from step (c), loaded with the natural substance capable of complexation with $Ni^{2+}$, $Cu^{2+}$ and/or $Fe^{2+}$ ions, with a solvent,
(e) desorption of the natural substance from the stationary phase of the IMAC device from step (c) or optionally from step (d), preferably by leading a solution containing one or more desorption agents through the IMAC device from step (c) or optionally from step (d),
(f) optionally separating the natural substance from the desorption agent,
(g) identifying the natural substance capable of complexation with $Ni^{2+}$, $Cu^{2+}$ and/or $Fe^{2+}$ ions.

The method according to the invention makes it possible to enrich and identify, selectively, from extracts of complex composition containing natural substances, those natural substances that are capable of complexation with $Ni^{2+}$, $Cu^{2+}$ and/or $Fe^{2+}$ ions.

Complexation with $Fe^{2+}$ ions is particularly relevant within the scope of the present invention, as $Fe^{2+}$ ions are a frequent contaminant of natural foodstuffs.

In addition, $Ni^{2+}$ ions are important, as these can remain in fats as traces of catalysts in hydrogenation of fats and in this way can enter foodstuffs.

The natural substance identified by the method according to the invention is preferably a natural substance suitable for human consumption, in particular an aroma or flavoring substance.

The aqueous, alcoholic or aqueous-alcoholic extract containing natural substances provided in step (a) and used in step (c) in the method according to the invention is preferably a plant extract or a food extract containing natural substances.

The extract containing natural substances provided in step (a) and used in step (c) in the method according to the invention is preferably a plant extract, which was obtained by extraction of one or more plant parts suitable for human consumption.

Particularly preferably it is an aqueous, alcoholic or aqueous-alcoholic extract containing natural substances, which was obtained by extraction of one or more plant parts, selected from the group consisting of stems, leaves, flowers, roots, seeds and fruits.

The aqueous, alcoholic or aqueous-alcoholic extract containing natural substances provided in step (a) and used in step (c) in the method according to the invention is generally a complex mixture and preferably contains 2, 3, 4, 5, 6, 7, 8, 9, 10 or more different aroma substances, and/or 2, 3, 4, 5 or more different flavoring ingredients.

The extract containing natural substances provided in step (a) and used in step (c) in the method according to the invention is for example an extract from green tea, malt or coffee beans.

WO 02/077024 discloses a protein that displays a metal ion binding activity on Ni and Cu ions. This protein was obtained from the oyster *Crassostrea gigas* and had a molecular weight of about 20 kDa or of about 31 kDa.

The natural substances identified or to be identified in the method according to the invention are preferably not proteins. Proteins within the scope of the present text are preferably to be understood as substances that are made up of more than 100 amino acids, preferably of more than 50 amino acids, in particular of more than 25 amino acids.

The natural substances identified or to be identified in the method according to the invention are preferably not substances with a molecular weight of 20 kDa or more, more preferably the natural substances have a molecular weight of less than or equal to 10 kDa, particularly preferably of less than or equal to 1000 g/mol.

The food extract containing natural substances used in the method according to the invention can be obtained from any material containing natural substances, which is usually consumed orally by humans.

Preferred food extracts are extracts of foods that are obtained from processed vegetable or animal products, such as for example roasted coffee beans, for which many of the substances with sensory action contained therein only form during roasting.

The extract containing natural substances provided in step (a) and used in step (c) in the method according to the invention is preferably an aqueous extract (i.e. an extract for which only water was used as extractant), or an alcoholic extract with one or more $C_1$-$C_4$ alcohols (i.e. an extract for which only a $C_1$-$C_4$ alcohol or a mixture of $C_1$-$C_4$ alcohols was used as extractant), and preferably ethanol, or an aqueous-alcoholic extract with one or more $C_1$-$C_4$ alcohols (i.e. an extract that was produced by extraction with a mixture consisting of water and $C_1$-$C_4$ alcohol(s)), and preferably an aqueous-ethanolic extract.

The adsorption in step (c) takes place by means of complexation (chelation, complexing) of natural substance and the metal ions bound to the stationary phase.

The solvent used in step (d) in the method according to the invention is preferably selected from the group consisting of pure water, ethanol, methanol and mixtures thereof. Solvents preferably used in step (d) are selected from the group consisting of pure water, preferably with ion-free water, and water-ethanol mixtures.

Preferably, in step (d), rinsing is carried out with a 5-fold, preferably with a 10-fold amount of solvent, relative to the empty volume of the IMAC device.

In the method according to the invention, in step (e) preferably a solution of a desorption agent is used, containing one or more compounds from the group consisting of EDTA, NaEDTA, $Na_2$EDTA, $CaNa_2$EDTA, oxalic acid, citric acid, phytic acid and ethylhexanoic acid.

Preferred desorption agents in step (d) are EDTA and EDTA salts, particularly preferably selected from the group consisting of EDTA, NaEDTA and $Na_2$EDTA. In particular in these cases the natural substances identified according to the invention are substances less strongly complexing with $Ni^{2+}$, $Cu^{2+}$ or $Fe^{2+}$ ions than EDTA and EDTA salts, which is particularly desirable and advantageous (see above).

The solution used in step (e) in the method according to the invention is preferably an aqueous, an ethanolic-aqueous or a methanolic-aqueous solution of a desorption agent.

Suitable methods for separating the natural substances capable of complexation with $Ni^{2+}$, $Cu^{2+}$ or $Fe^{2+}$ ions from the desorption agent in step (f) are known by a person skilled in the art, for example HPLC (high-performance liquid chromatography). The HPLC separation is preferably carried out using a C-18 phase and a HILIC phase (HILIC: hydrophilic interaction chromatography; aqueous normal-phase chromatography).

The separated and isolated natural substances capable of complexation with $Ni^{2+}$, $Cu^{2+}$ or $Fe^{2+}$ ions are finally identified in step (g), i.e. their structure is elucidated. This is preferably done by mass spectroscopy (MS) and/or by NMR spectroscopy.

With respect to further preferred embodiments of the method according to the invention, the respective embodiments of the respective process steps described above as preferable or particularly preferable apply correspondingly.

In a particularly preferred embodiment, the present invention relates to a method of identifying a natural substance suitable for human consumption, in particular an aroma or flavoring substance, which is capable of complexation with $Fe^{2+}$, characterized by the following steps:

(a) providing an aqueous, ethanolic or aqueous-ethanolic extract containing natural substances, (b) providing a device containing a stationary phase loaded with $Fe^{2+}$ ions, which is suitable for immobilized metal affinity chromatography (IMAC) (IMAC device), (c) leading the extract containing natural substances from step (a) through a device from step (b), so that the natural substance capable of complexation with $Fe^{2+}$ ions is adsorbed on the stationary phase of the IMAC device, (d) rinsing the stationary phase of the IMAC device from step (c) loaded with the natural substance capable of complexation with $Fe^{2+}$ ions, with a solvent selected from the group consisting of pure water and water-ethanol mixtures, (e) desorption of the natural substance from the stationary phase of the IMAC device from step (d) by leading a solution containing EDTA, NaEDTA and/or $Na_2EDTA$ through the IMAC device from step (d), (f) separating the natural substance from the desorption agent EDTA, NaEDTA and/or $Na_2EDTA$, (g) identifying the natural substance capable of complexation with $Ni^{2+}$, $Cu^{2+}$ and/or $Fe^{2+}$ ions, preferably by mass spectroscopy and/or NMR spectroscopy.

The fluids used in each case in the method according to the invention are led, preferably pumped, over the stationary phase, preferably in each case with flow rates in the range 0.5-20 ml/min, preferably 1-10 ml/min. These figures apply to IMAC devices, in particular IMAC columns, with a (column) volume of 1-20 ml.

The method according to the invention can be carried out with various IMAC devices. IMAC materials are known by a person skilled in the art and are commercially available, for example as IMAC-Select Affinity Gel (manufacturer: Sigma-Aldrich) or as IMAC columns without metal ion loading, for example under the names IMAC Sepharose 6 Fast Flow (manufacturer: GE Healthcare), e.g. in the form of the HiTrap IMAC FF columns.

The parameters for carrying out the method according to the invention depend within certain limits on the IMAC device used in each case, in particular on the dimensioning and the material used for the stationary phase. A person skilled in the art can easily determine these parameters, taking into account the manufacturer's instructions and the manufacturer's manual, and carry out the method according to the invention.

Some preferred embodiments of the method according to the invention are explained below.

Preferably the method according to the invention is carried out at room temperature (20° C.) and taking into account the information in the manufacturer's manual.

Before loading the IMAC device with metal ions, preferably the stationary phase of the IMAC device is first rinsed with water, preferably ion-free water.

Then the solid adsorbent, i.e. the stationary phase, of the IMAC device is loaded with $Ni^{2+}$, $Cu^{2+}$ or $Fe^{2+}$ ions. For this, preferably a 0.025-0.25 M, preferably a 0.1 M, metal cation solution of an $Ni^{2+}$, $Cu^{2+}$ or $Fe^{2+}$ salt is prepared and contacted with the stationary phase that is to be loaded, wherein the metal cations are bound by the chelating ligands of the stationary phase.

Preferred $Ni^{2+}$, $Cu^{2+}$ or $Fe^{2+}$ salts are water-soluble salts of these metal ions, and the preferred $Fe^{2+}$ salt is $Fe(NH_4)_2(SO_4)_2 \times 6H_2O$.

Loading of the stationary phase with the metal cation solution is preferably carried out with an amount of metal cation solution of at least half a volume fraction, relative to the empty volume of the IMAC device.

Then the stationary phase loaded with $Ni^{2+}$, $Cu^{2+}$ or $Fe^{2+}$ ions is rinsed with water, preferably with ion-free water, or an ethanolic-aqueous solvent medium, in order to remove the excess, unbound $Ni^{2+}$, $Cu^{2+}$ or $Fe^{2+}$ ions. It is preferably rinsed with an at least 5-fold amount of water or ethanolic-aqueous solvent medium, relative to the empty volume of the IMAC device.

The extract containing natural substances to be investigated is preferably used as diluted aqueous solution or as diluted aqueous-ethanolic solution.

The extract containing natural substances is preferably filtered on a membrane filter, preferably with a pore size of 0.45 μm, before it is led through the IMAC device.

Then the extract containing natural substances is put in the IMAC device and is led through the IMAC device, preferably in double, preferably in three times the amount, relative to the empty volume of the IMAC device.

As the extract containing natural substances is led through the adsorbent loaded with metal cations, the natural substances capable of complexation with $Ni^{2+}$, $Cu^{2+}$ or $Fe^{2+}$ ions are held back by the stationary phase and remain there (adsorption).

The other compounds of the extract, not complexed by the metal cations of the stationary phase, are then removed by rinsing with the corresponding solvent medium, preferably with distilled water or ethanolic-aqueous solvent media.

It is then preferably rinsed with a 10-fold amount of solvent, relative to the empty volume of the IMAC device.

For detaching the natural substances capable of complexation with $Ni^{2+}$, $Cu^{2+}$ or $Fe^{2+}$ ions from the stationary phase, the adsorbent is rinsed with a solution containing one or more desorption agents, preferably an aqueous solution of EDTA, NaEDTA or $Na_2EDTA$.

The concentration of the desorption agent is preferably in the range of 10-100 mM.

Preferably it is rinsed with a 5-fold, preferably a 10-fold amount, of a solution containing one or more desorption agents, relative to the empty volume of the IMAC device.

The desorption agent separates the bond between the chelating ligands bound covalently to the adsorbent and the metal cations, by itself binding to the metal cations.

Therefore the natural substances capable of complexation with $Ni^{2+}$, $Cu^{2+}$ or $Fe^{2+}$ ions from the extract containing natural substances can no longer be retained by the stationary phase and are rinsed out in this rinsing operation (elution).

The mixture obtained, containing desorption agent, natural substances capable of complexation with $Ni^{2+}$, $Cu^{2+}$ or $Fe^{2+}$ ions and optionally $Ni^{2+}$, $Cu^{2+}$ or $Fe^{2+}$ ions, is then separated and analyzed.

Suitable methods for separating the natural substances capable of complexation with $Ni^{2+}$, $Cu^{2+}$ or $Fe^{2+}$ ions and desorption agent are for example HPLC (high-performance liquid chromatography) using a C-18 phase and a HILIC phase (HILIC: hydrophilic interaction chromatography; aqueous normal-phase chromatography).

If the natural substances capable of complexation with $Ni^{2+}$, $Cu^{2+}$ or $Fe^{2+}$ ions are retained by the C-18 phase, the desorption agent is preferably separated by solid-phase extraction (SPE) on a C-18 phase.

If the natural substances capable of complexation with $Ni^{2+}$, $Cu^{2+}$ or $Fe^{2+}$ ions are retained by the HILIC phase, the desorption agent is preferably separated by preparative HPLC (PHPLC) on a HILIC phase.

Once the natural substances capable of complexation with $Ni^{2+}$, $Cu^{2+}$ or $Fe^{2+}$ ions have been separated, they are then analyzed and identified, preferably identified by mass spectroscopy (e.g. LC-MS) and by NMR spectroscopy.

The natural substances capable of complexation with $Ni^{2+}$, $Cu^{2+}$ and/or $Fe^{2+}$ ions, identified with the method according to the invention, can be used specifically for sensory stabilization of oxidation-sensitive orally consumable preparations.

Suitable criteria for the extent of oxidation are for example the peroxide number, measurement (of the amount) of volatile aldehydes (in particular of n-hexanal) and measurement (of the amount) of malonic dialdehyde.

The present invention further relates to the use of a stationary phase loaded with $Ni^{2+}$, $Cu^{2+}$ and/or $Fe^{2+}$ ions, which is suitable for immobilized metal affinity chromatography (IMAC), for identifying a natural substance that is capable of complexation with $Ni^{2+}$, $Cu^{2+}$ and/or $Fe^{2+}$ ions.

A preferred use according to the invention is characterized in that the natural substance is a natural substance suitable for human consumption, and preferably is selected from the group consisting of aroma substances and flavoring ingredients.

The method according to the invention and a device that is particularly suitable for carrying out the method are described in more detail below on the basis of examples, without this limiting the scope of protection relative to the patent claims.

EXAMPLE 1

Method—Procedure for Immobilized Metal Affinity Chromatography (IMAC)

All tests were carried out at room temperature and taking into account the information in the manufacturer's manual of the IMAC column.

IMAC Sepharose® 6 Fast Flow material from the company GE Healthcare (General Electric Healthcare) was used as stationary phase (solid adsorbent) for the IMAC method.

This matrix is a spherical, crosslinked 6% agarose with an average particle size of 90 μm. Chelating ligands are bound covalently to this matrix.

IMAC columns with 1 ml column volume and with 20 ml column volume were used. The flows were adjusted so that the flow rates were 1.3 ml/min in the case of the IMAC columns with 1 ml column volume (at max. p of 0.30 MPa) and 6.3 ml/min in the case of the IMAC columns with 20 ml column volume (at max. p of 0.15 MPa).

After rinsing the stationary phase with five times the column volume of distilled water, the stationary phase was loaded with $Fe^{2+}$ ions.

An aqueous 0.1 M $Fe^{2+}$ solution of $Fe(NH_4)_2(SO_4)_2 \times 6H_2O$ and distilled water was led through the adsorbent, thus loading the adsorbent with $Fe^{2+}$ ions.

Then the stationary phase loaded with $Fe^{2+}$ ions was rinsed again with five times the column volume of distilled water, to remove the excess/unbound metal cations.

Distilled water or ethanolic-aqueous solvent media are preferably used as solvent media for the extract containing natural substances, depending on the solubility of the extract.

The extract containing natural substances to be investigated in each case (also called natural substance extract hereinafter) was used as diluted aqueous solution or as diluted aqueous-ethanolic solution.

All tests were carried out with membrane-filtered (0.45 km) natural substance extracts.

This natural substance extract was then led through the adsorbent loaded with metal cations and the compounds with $Fe^{2+}$-ion-complexing properties were retained by the stationary phase (adsorption).

The other compounds of the natural substance extract, not complexed by the $Fe^{2+}$ ions of the stationary phase, were then rinsed from the IMAC column by rinsing with ten times the column volume of distilled water.

For detaching the natural substances capable of complexation with $Fe^{2+}$ ions from the stationary phase, the adsorbent was rinsed from the IMAC column with ten times the column volume of aqueous 50 mM EDTA solution (prepared from $Na_2EDTA \times 2H_2O$ and distilled water).

The resultant mixture of EDTA, $Fe^{2+}$ and the natural substances capable of complexation with $Fe^{2+}$ ions was analyzed using HPLC (high-performance liquid chromatography) using a C-18 phase and a HILIC phase (HILIC: hydrophilic interaction chromatography; aqueous normal-phase chromatography).

If the complexing compounds were retained by the C-18 phase, the EDTA was separated by solid-phase extraction (SPE) on a C-18 phase. If the compounds were retained by the HILIC phase, EDTA separation was carried out by preparative HPLC on a HILIC phase.

The natural substances were then analyzed by LC-MS and their structure was identified by NMR spectroscopy.

EXAMPLE 2

Green Tea Extract

The procedure followed was as described in Example 1. For carrying out the method with green tea extract, the extract was used as diluted aqueous solution of green tea (10 mg/ml) (10 mg extract dissolved in 1 ml water). The adsorbent was loaded using a 0.1 M aqueous $Fe^{2+}$ solution of $Fe(NH_4)_2(SO_4)_2 \times 6H_2O$ and water. After loading, it was rinsed with distilled water and then the aqueous solution of the green tea extract was led through the adsorbent loaded with $Fe^{2+}$ ions. After rinsing with water, the complexing natural substances were eluted with 50 mM EDTA solution. Subsequent HPLC analysis showed that the compounds contained are retained on a C-18 phase, therefore SPE was carried out on a C-18 phase for separating the EDTA. In the subsequent analysis, epigallocatechin gallate was identified as the $Fe^{2+}$-complexing natural substance.

EXAMPLE 3

Malt Extract

The procedure followed was as described in Example 1. For carrying out the method with malt extract, the extract was used as diluted aqueous solution (10 mg/ml). Loading of the adsorbent was carried out as in Example 2, once again with $Fe^{2+}$ ions. After loading, it was rinsed with distilled water and then the aqueous solution of the malt extract was led through the material loaded with $Fe^{2+}$ ions. After rinsing with water, the complexing natural substances were eluted with 50 mM EDTA solution. Subsequent HPLC analysis showed that the compounds contained are retained on a HILIC phase. For preliminary separation of a large part of the EDTA, ethanol was added to this solution, which caused precipitation of the EDTA, so that the EDTA could be filtered off. Then the remaining EDTA was separated by PHPLC (preparative HPLC) on the HILIC phase using water and acetonitrile.

EXAMPLE 4

Coffee Extract

The procedure followed was as described in Example 1. For carrying out the method with coffee extract, the extract was used as diluted aqueous solution, prepared from 5 g coffee powder and 25 g boiling water. Loading of the adsorbent was carried out as in Example 2, once again with $Fe^{2+}$ ions. After loading, it was rinsed with distilled water and then the aqueous solution of the coffee extract was led through the adsorbent loaded with $Fe^{2+}$ ions. After rinsing with water, the complexing compounds were eluted with 50 mM aqueous EDTA solution. Subsequent HPLC analysis showed that the compounds contained are retained on a HILIC phase. For preliminary separation of a large part of the EDTA, ethanol was added to this solution, which caused precipitation of the EDTA, so that the EDTA could be filtered off. Then the remaining EDTA was separated by PHPLC (preparative HPLC) on the HILIC phase using water and acetonitrile.

The invention claimed is:

1. A method of identifying a natural substance that is capable of complexation with $Ni^{2+}$, $Cu^{2+}$ and/or $Fe^{2+}$, comprising:
   (a) providing an aqueous, alcoholic or aqueous-alcoholic extract comprising natural substances,
   (b) providing a device comprising a stationary phase loaded with $Ni^{2+}$, $Cu^{2+}$ and/or $Fe^{2+}$ ions, which is suitable for immobilized metal affinity chromatography (IMAC) (IMAC device),
   (c) leading the extract comprising natural substances from (a) through the device from (b), so that the natural substance capable of complexation with $Ni^{2+}$, $Cu^{2+}$ and/or $Fe^{2+}$ ions is adsorbed on the stationary phase of the IMAC device,
   (d) optionally rinsing the stationary phase of the IMAC device from (c), loaded with the natural substance capable of complexation with $Ni^{2+}$, $Cu^{2+}$ and/or $Fe^{2+}$ ions, with a solvent,
   (e) desorption of the natural substance from the stationary phase of the IMAC device from (c), or optionally from (d) is by leading a solution containing one or more desorption agents through the IMAC device from step (c), or optionally from step (d),
   (f) optionally separating the natural substance from the desorption agent, and
   (g) identifying the natural substance capable of complexation with $Ni^{2+}$, $Cu^{2+}$ and/or $Fe^{2+}$ ions,
      wherein the extract comprising natural substances provided in (a) and used in (c) is a plant extract, obtained by extraction of one or more plant parts suitable for human consumption and wherein the natural substance to be identified is not a protein, and has a molecular weight of less than or equal to 1000 g/mol.

2. The method as claimed in claim 1, wherein the extract comprising natural substances provided in (a) and used in (c) is a plant extract, which was obtained by extraction of one or more plant parts selected from the group consisting of stems, leaves, flowers, roots, seeds, and fruits.

3. The method as claimed in claim 1, wherein the extract comprising natural substances provided in (a) and used in (c) is an aqueous extract, or
   an alcoholic extract with one or more $C_1$-$C_4$ alcohols, or
   an aqueous-alcoholic extract with one or more $C_1$-$C_4$ alcohols.

4. The method as claimed in claim 1, wherein the solvent used in (d) is selected from the group consisting of water, ethanol, methanol and mixtures thereof.

5. The method as claimed in claim 1, wherein in (e), a solution of a desorption agent is used that comprises one or more compounds selected from the group consisting of EDTA, NaEDTA, $Na_2$EDTA, $CaNa_2$EDTA, oxalic acid, citric acid, phytic acid and ethylhexanoic acid.

6. The method as claimed in claim 1, wherein the solution used in (e) is an aqueous, an ethanolic-aqueous or a methanolic-aqueous solution of a desorption agent.

7. The method as claimed in claim 1, wherein in (f), the natural substance is separated from the desorption agent by means of extraction or by means of chromatography.

8. The method of claim 1, wherein desorption of the natural substance from the stationary phase of the IMAC device comprises leading a solution containing one or more desorption agents through the IMAC device from (c) or optionally from step (d).

9. The method as claimed in claim 3, wherein the extract comprising natural substances provided in (a) and used in (c)
   is an aqueous extract, or
   an ethanol, or
   an aqueous-ethanolic extract.

10. The method as claimed in claim 2, wherein the solvent used in (d) is selected from the group consisting of water, ethanol, methanol and mixtures thereof.

11. The method as claimed in claim 9, wherein the solvent used in (d) is selected from the group consisting of water, ethanol, methanol and mixtures thereof.

12. The method as claimed in claim 4, wherein in (e), a solution of a desorption agent is used that comprises one or more compounds selected from the group consisting of EDTA, NaEDTA and $Na_2$EDTA.

13. The method as claimed in claim 5, wherein in (e), a solution of a desorption agent is used that comprises one or more compounds selected from the group consisting of EDTA, NaEDTA and $Na_2$EDTA.

14. The method as claimed in claim 5, wherein the solution used in (e) is an aqueous, an ethanolic-aqueous or a methanolic-aqueous solution of a desorption agent.

15. The method as claimed in claim 6, wherein the solution used in (e) is an aqueous, an ethanolic-aqueous or a methanolic-aqueous solution of a desorption agent.

16. The method as claimed in claim 7, wherein in (f), the natural substance is separated from the desorption agent by means of SPE, liquid/liquid separation, precipitation or by means of gel chromatography, HPLC or HILIC (hydrophilic interaction chromatography; aqueous normal-phase chromatography).

* * * * *